United States Patent
Eigler et al.

(10) Patent No.: US 8,172,856 B2
(45) Date of Patent: May 8, 2012

(54) METHODS AND APPARATUS FOR ATRIOVENTRICULAR VALVE REPAIR

(75) Inventors: Neal L. Eigler, Pacific Palisades, CA (US); Matthew J. Price, Del Mar, CA (US); Robert J. Siegel, Beverly Hills, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 571 days.

(21) Appl. No.: 10/628,880

(22) Filed: Jul. 28, 2003

(65) Prior Publication Data

US 2004/0059351 A1  Mar. 25, 2004

Related U.S. Application Data

(60) Provisional application No. 60/400,840, filed on Aug. 2, 2002.

(51) Int. Cl.
*A61B 17/10* (2006.01)
*A61B 17/04* (2006.01)

(52) U.S. Cl. .................................. 606/139; 606/148
(58) Field of Classification Search ................. 623/2.36; 606/139, 144, 148, 232
See application file for complete search history.

(56) References Cited

U.S. PATENT DOCUMENTS

| | | | |
|---|---|---|---|
| 4,777,951 A * | 10/1988 | Cribier et al. ................. 606/194 |
| 5,201,880 A | 4/1993 | Wright et al. | |
| 5,609,598 A * | 3/1997 | Laufer et al. ................. 606/142 |
| 5,626,588 A * | 5/1997 | Sauer et al. ................... 606/144 |
| 5,716,367 A | 2/1998 | Koike et al. | |
| 6,029,671 A | 2/2000 | Stevens et al. | |
| 6,051,014 A | 4/2000 | Jang | |
| 6,117,144 A * | 9/2000 | Nobles et al. ................. 606/144 |
| 6,117,145 A | 9/2000 | Wood et al. | |
| 6,136,010 A * | 10/2000 | Modesitt et al. .............. 606/144 |
| 6,165,183 A * | 12/2000 | Kuehn et al. .................. 606/139 |
| 6,197,043 B1 | 3/2001 | Davidson | |
| 6,206,893 B1 | 3/2001 | Klein et al. | |
| 6,269,819 B1 | 8/2001 | Oz et al. | |
| 6,287,321 B1 | 9/2001 | Jang | |

(Continued)

FOREIGN PATENT DOCUMENTS

| | | |
|---|---|---|
| WO | WO 00/60995 | 10/2000 |
| WO | WO 01/26557 A1 | 4/2001 |
| WO | WO 03/049619 | 6/2003 |
| WO | WO 2004/012583 | 2/2004 |

OTHER PUBLICATIONS

Michael Black MD, Division of Pediatric Cardiac Surgery, Standford University School of Medicine, California, USA, Minimally Invasive Pediatric Cardiac Surgery, Online Article in 4 pages.

(Continued)

*Primary Examiner* — Corrine M McDermott
*Assistant Examiner* — Melissa Ryckman
(74) *Attorney, Agent, or Firm* — Knobbe, Martens, Olson & Bear, LLP

(57) ABSTRACT

Methods and devices are disclosed for minimally invasive procedures in the heart. In one application, a catheter is advanced from the left atrium through the mitral valve and along the left ventricular outflow tract to orient and stabilize the catheter and enable a procedure such as a "bow tie" repair of the mitral valve. Right heart procedures are also disclosed.

21 Claims, 15 Drawing Sheets

U.S. PATENT DOCUMENTS

| | | | |
|---|---|---|---|
| 6,312,446 B1 | 11/2001 | Huebsch et al. | |
| 6,312,447 B1 | 11/2001 | Grimes | |
| 6,325,067 B1 | 12/2001 | Sterman et al. | |
| 6,328,757 B1 | 12/2001 | Matheny | |
| 6,752,813 B2 * | 6/2004 | Goldfarb et al. | 606/139 |

OTHER PUBLICATIONS

Ethicon Wound Closure Manual—Chapter 6, Research and Development at Ethicon, Inc.—An Ongoing Process of Change and Improvement, Online at www.ethiconinc.com in 4 pages.

*Mitral Valve Repair or Replacement on the Beating Heart*, Borut Gersak, MD, Ph.D., The Heart Surgery Forum #2000-1989, Jun. 8, 2000, pp. 232-237, 2000 Forum Multimedia Publishing, LLC.

Supplementary European Search Report for Application No. EP 03767041.1 dated Apr. 21, 2008 in 6 pages.

Bhargava et al. Biosense Left Ventricular Electromechanical Mapping. Asian Cardiovasc Thorac Ann 1999; 7:345-52.

Perclose A-T, 6F Suture-Mediated Closure (SMC) System, Instructions for Use distributed in the U.S. by Abbott Laboratories, Inc. © 2002, 2006 Abbott Laboratories in 11 pages.

* cited by examiner

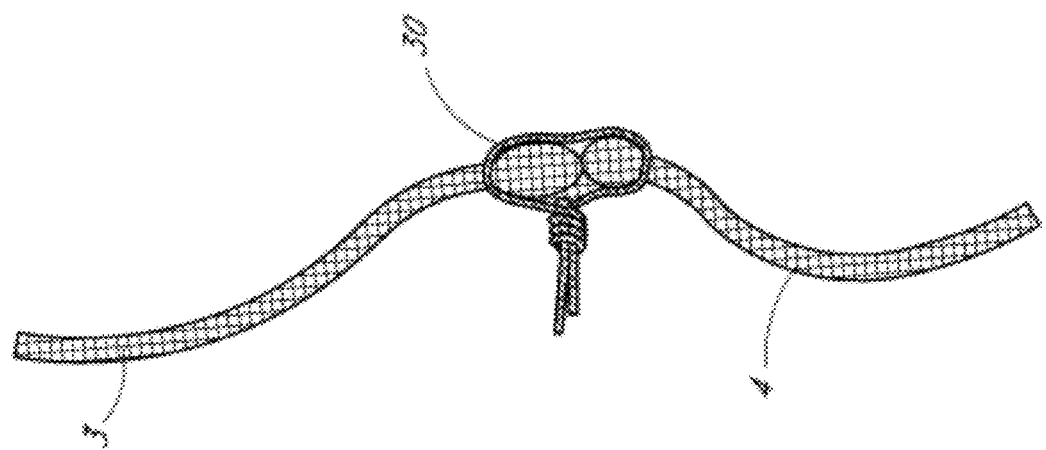
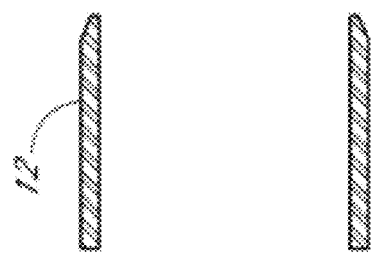
FIG. 15

METHODS AND APPARATUS FOR ATRIOVENTRICULAR VALVE REPAIR

This application claims priority under 35 U.S.C. §119 to U.S. Provisional patent application serial No. 60/400,840, filed Aug. 2, 2002, the disclosure of which is incorporated in its entirety herein by reference.

FIELD OF THE INVENTION

The present invention relates generally to the field of heart valve repair. In a preferred embodiment, the invention relates to heart valve repair for patients suffering from mitral and/or triscupid valve regurgitation. It is a method and apparatus for repairing a cardiac atrioventricular valve consisting of a catheter(s)/guidance system that uses the position of a leaflet immobilization device in the ventricular outflow tract as a means of orientation so that immobilization of the leaflets will occur without interfering with the papillary muscles, chordal structures, or other cardiac structures. The method and apparatus provides a means for manipulating a catheter/apparatus to independently capture and immobilize the leaflets of the heart at the optimal central location, and a means for fastening these immobilized leaflets together to accomplish a "bow-tie" repair.

BACKGROUND OF THE INVENTION

A major type of heart disease is valvular insufficiency, also called valvular regurgitation, which is characterized by the improper closing of a heart valve. A heart valve consists of a number of leaflets—either two or three—that swing open to allow blood to flow forward (anterograde) out of a heart chamber, and then swing closed to form a tight seal, preventing blood from leaking backwards (retrograde). Valvular insufficiency may result from a variety of problems with the components which make up the valve—for example, the leaflets themselves may degenerate, the tissue cords which tether the leaflets to muscles within the heart may break, or the ring of tissue within which the valve is seated (called the "annulus") may expand after heart attacks or from congestive heart failure. Each of these problems leads to a common element in valvular regurgitation: when closed, the edges of the valve leaflets no longer fit snuggly next to each other and allow retrograde flow.

Mitral regurgitation (MR) (insufficiency of the valve which connects the left atrium with the left ventricle of the heart) and tricuspid regurgitation (insufficiency of the valve which connects the right atrium with the right ventricle of the heart) contribute significantly to cardiovascular morbidity and mortality. MR is a debilitating disease that can lead to serious complications and possible death. Its symptoms include shortness of breath, rapid respirations, palpitations, chest pain, and coughing. MR also leads to infective endocarditis, heart failure, pulmonary edema, stroke, arterial embolus, and arrhythmias, including atrial fibrillation and lethal ventricular arrhythmias. Detection and prompt effective treatment of MR leads to higher survival rates, decreased complications, and increased comfort for patients.

Currently, the only method of definitively repairing valvular regurgitation is open-heart surgery: In this procedure, the patient is first anesthetized and then subject to a thoracotomy. Access to the patient's heart is achieved by making a large incision, retracting the skin, muscle, and bony structures. The surgeon must stop the beating of the heart and cut it open to directly visualize the valve. The surgeon then may repair the valve surgically, or remove the valve and implant a prosthetic valve replacement. This requires placing the patient on cardiopulmonary bypass, which is a machine that circulates oxygenated blood throughout the body in place of the working heart and lungs.

Although open-heart surgery is a successful method of repairing or replacing faulty heart valves, it poses a significant risk to the well being of the patient, including death, severe injury, and disability. There is a risk of ischemic or other damage to the heart and other vital organs resulting from the discontinuance of the heart's normal function. The heart-lung machine may also cause abnormalities of the patient's circulatory, respiratory, hematologic and neurologic systems. There is a risk of stroke and other consequences from emboli released into the blood during the surgery and during initiation of cardiopulmonary bypass. There is a risk of heart attack. Significant damage occurs to the tissues and bone retracted from the patient's chest while gaining access to the heart. Post-operative complications such as wound infection, pneumonia, and venous thrombosis occur because of the extent of incisions and the patient's debilitated state. Consequently, a patient's recovery can be painful, discomforting, long in duration, and costly.

A minimally invasive, beating-heart procedure that would not expose the patient to these risks is therefore desirable. Moreover, a limited surgical approach or percutaneous approach would decrease or eliminate the tissue trauma that occurs from the extensive incisions of open-heart surgery, sparing patients pain, improving recovery time, and decreasing post-operative complications.

A very large population exists that would benefit from an alternative method of valve repair. Approximately 10% of coronary artery bypass surgeries include mitral valve repair or replacement, which amounts to 75,000 to 100,000 of such procedures per year world-wide. In addition, significant MR and/or TR complicate 30-60% of patients with congestive heart failure, contributing to their impaired cardiac function and causing significant morbidity. However, because of the significant risks involved in open-heart surgery, many of the patients are unable to undergo valve repair. Thus, a successful percutaneous or minimally-invasive method of valve repair on the beating heart would have extraordinary clinical benefit.

No one, however, has successfully repaired the mitral valve of the human heart with a minimally invasive, beating-heart procedure. Several factors are responsible for this. First, the heart and its associated valves are not directly visualized or accessible. One can use imaging techniques such as fluoroscopy or echocardiography, but these provide a two-dimensional image and a limited field of view. Second, it is extremely difficult to immobilize the rapidly moving heart valve leaflets for repair purposes while the heart is beating. Not only are the leaflets moving back and forth rapidly, but also they each have a different shape and geometry. Thus, no single device or methodology has successfully been used to repair heart valves in a minimally invasive manner on a beating heart.

One method of surgical repair of the mitral valve, called the "bow-tie" repair (also referred to as the "edge-to-edge" repair), especially lends itself to a percutaneous or minimally-invasive approach. In this technique, the patient is placed on cardiopulmonary bypass, the heart is stopped and incised to expose the mitral valve apparatus, and a single edge-to-edge suture is placed through the edges of the valve leaflets, thereby apposing the anterior and posterior leaflets and resulting in a "double-orifice" valve. This surgical technique has led to satisfactory reduction of mitral regurgitation (MR) with few re-operations and excellent hemodynamic results. A successful minimally-invasive or percutaneous device and method that would allow for the placement of such a suture or another apposing element by remotely manipulating a fastening device through the moving valve leaflets of the beating heart in a reliable and predictable manner would be a medical breakthrough.

There are several obstacles that such a device must overcome. Each valve leaflet moves independently, swinging open and closed as many as 40 to 120 times a minute (or 1 to 2 times a second). Blood is surging back and forth through the valve at velocities often greater than 3 meters per second. Each valve leaflet has a different shape, for example, the anterior leaflet of the mitral valve is long and relatively narrow, while the posterior leaflet is shallow and wide. The valve apparatus on the ventricular side of the valve—consisting of primary, secondary, and tertiary chordae tendinae and the papillary muscles—makes the manipulation of devices in this area difficult, and consequently the successful deployment of the device requires correctly negotiating the pathway through the valve without becoming entrapped within the cardiac structures and/or damaging them. The suture or "fastener" must incorporate enough leaflet tissue to prevent leaflet tearing and secure leaflet capture at the optimal location.

A number of patents describe devices and methods for placing a suture within tissue at a distance. U.S. Pat. No. 6,206,893 details a device and method for suturing of internal puncture sites, and U.S. Pat. No. 6,117,145 provides a method and device for providing hemostasis at vascular penetration sites. These patents describe devices and methods for stitching a suture through a punctured blood vessel from a remote site that is not under direct visual observation and thereby apposing the edges of the blood vessel wall. These described methods and devices are insufficient for properly and optimally capturing and fastening cardiac valve leaflets, because they do not describe methods or apparatuses that are sufficient to ensure the proper alignment with intracardiac structures, the independent immobilization of the mobile valve leaflets, and the fastening of tissues with specific leaflet geometry.

A number of patents address minimally invasive or percutaneous mitral and tricuspid valve repair, utilizing a variation of the concept of a "suture at a distance" derived from the open-heart "bow-tie" technique. U.S. Pat. No. 6,165,183 describes an approach to valve repair involving the performance of an edge-to-edge fastening of opposing heart valve leaflets through a catheter entering the heart. This patent describes a catheter to place a clip button on the two leaflets, and describes various embodiments of ways a clip can fasten two pieces of tissue together at a distance. No attention is paid however to the requirements of placing the clip within a cardiac valve of a living patient, specifically, how moving valves can be grasped and immobilized; how the device is oriented with regard to the asymmetric leaflets and other cardiac structures so that a proper clip position is obtained; and a remedy for improper clip position. Thus, U.S. Pat. No. 6,165,183 does not describe a clinically feasible device or method for cardiac valve repair. U.S. Pat. No. 6,269,819 describes "an apparatus for the repair of a cardiovascular valve having leaflets comprising a grasper capable of grabbing and coapting the leaflets of the valve." It is based on the concept of a "bow-tie" repair performed at a distance. There is no description of a methodology of placing the device across the valve and avoiding cardiac structures. There is no description of how the grasper—which essentially pinches the two leaflets together—can simultaneously catch the two independently, rapidly moving leaflets in a reliable fashion or at the optimal location, other than on the stopped heart with the patient on cardiopulmonary bypass. As such, U.S. Pat. No. 6,269,819 does not provide a clinically feasible or optimal approach to minimally invasive valve repair.

SUMMARY OF THE INVENTION

Disclosed herein is a method and apparatus for performing valve repair on a beating heart in a minimally invasive or percutaneous manner by introducing at a distance a suture tie or fastener that will appose the leaflet edges and create a double-orifice valve. Importantly, the method and apparatus uniquely provide for proper orientation within the heart to approach the asymmetric atrioventricular valve leaflets, enable the independent capture of the moving leaflets, and provide for the release and re-securing of the leaflets if the initial position or fixation is not optimal. The apparatus and methods described are optimized for mitral valve repair, but it would be apparent to one skilled in the art, such as interventional cardiologists and cardiothoracic surgeons, that minor changes in the device or techniques will also optimize the procedure for tricuspid valve repair as well.

The apparatus consists of a catheter-based system for percutaneous advancement and placement within the human heart consisting of heart-valve leaflet immobilization and fixation devices housed within one or more catheters. In a preferred embodiment, the device/apparatus consists of (a) an orientation catheter which contains a central lumen for a guide wire (b) one or more guide wires (c) a device Housing Catheter (HC) and (d) a Valve Immobilization Catheter (VIC) which contains the Leaflet Immobilization Apparatus. In alternative embodiments of the device, the orientation catheter, device housing catheter, and valvular immobilization catheter may be incorporated into one or more catheters that may contain central lumens for guide wires.

The catheters each have a proximal end and a distal end. They may contain a central lumen that is designed for placement over a guide wire and they may be torqueable and flexible as required for their advancement via the left atrium across the mitral valve, through the left ventricular outflow tract, and across the aortic valve, where the proximal end may then sit in the ascending aorta. The route of the catheter thereby provides a means of predictable orientation of the catheter with respect to the papillary muscles, the anterior leaflet, and the posterior leaflet of the mitral valve. The shape of the catheter thus formed acts as a fulcrum about which the catheter can be easily manipulated with respect to the individual valve leaflets.

The orientation catheter has an inflatable balloon at its distal end and a central lumen for a guide wire, and is advanced into the ascending aorta from the left atrium. The placement of the catheter allows for the easy advancement of the other elements of the device through the mitral valve orifice, its chordal attachments, and the papillary muscles without getting entangled in these structures. A guide wire may be advanced through the orientation catheter, allowing other catheters of the system (such as the Housing Catheter) to be exchanged over this wire so that the position of the distal aspect of the device in the ascending aorta is maintained.

The Housing Catheter (HC) contains a central lumen through which the Valve Immobilization Catheter (VIC) can be advanced. The HC contains two ports within proximity to the valve leaflets when the device is properly positioned within the heart. These ports are openings that allow for the deployment of leaflet immobilization supports and fixation devices that secure the valve leaflets. These supports and fixation devices are contained within the Valve Immobilization Catheter that is advanced within the Housing Catheter.

The Valve Immobilization Catheter has a semi-rigid portion that contains the leaflet immobilization apparatus. The leaflet immobilization apparatus contains two asymmetric leaflet immobilization supports, one optimized for the anterior leaflet and one optimized for the posterior leaflet with respect to size, angulation, and positioning along the length of the catheter system. The leaflet immobilization apparatus also contains two fixating members that allow for the independent securing of the individual leaflets.

The method of device operation involves introducing the catheter apparatus into the left atrium through a sheath placed percutaneously through the right femoral vein in the conventional transseptal cardiac catheterization approach. A guide wire is manipulated through the sheath across the mitral valve, through the left ventricular outflow tract (LVOT), and into the ascending aorta. The positioning of the guide wire may be aided by first using a balloon floatation catheter (the "orientation catheter") to cross the mitral valve and enter the ascending aorta. The Housing Catheter and, within this, the VIC are advanced over the wire into the ascending aorta. Now, given the anatomical fact that the anterior leaflet of the mitral valve also forms the left ventricular outflow tract, the catheter position has provided a specific orientation with respect to the asymmetric valve leaflets, automatically aligning the device between the chordal attachments to the papillary muscles. The operator then engages the valve leaflets by remotely actuating the deployment of the anterior leaflet immobilization support (LIS) and then does the same with the posterior LIS. Once the proper alignment of both is confirmed by fluoroscopic and/or transthoracic, transesophageal, or intracardiac echocardiographic visualization, the leaflets are fastened together by fixating material upon further remote actuation by the operator. The adequacy of the repair is assessed by fluoroscopy and/or echocardiography and the fastening is revised if needed. One then pulls the fastening material tight, withdraws the catheter system, and ties the fastening material, thereby apposing the edges of the valve leaflets and completing the valve repair.

In alternative embodiments, the orientation catheter, Housing Catheter, Valve Immobilization Catheter, and Leaflet Immobilization Apparatus may be incorporated into one or more catheters, each of which may or may not contain an inflatable balloon at its distal end.

In alternative embodiments, the catheters of the system may contain a pre-shaped curve to assist in advancing them through the left ventricle into the aorta.

In another embodiment, the sheath may be placed across the interatrial septum, through the left ventricle, and into the aortic root, and then the sheath is withdrawn exposing the immobilization and fixation components of the device.

In another embodiment, the fixating members may deploy a crimp or staple to appose the leaflet edges in an edge-to-edge repair.

In another method aspect, the device may be introduced into the left atrium through an incision the the left atrium or through a direct puncture of a pulmonary vein; or through an incision into the right atrium and then into the left atrium through a trans-septal puncture; or percutaneously through an internal jugular vein and across the inter-atrial septum; or through a femoral vein and across the inter-atrial septum; or any other central venous access that provides a route to the right atrium and then across the inter-atrial septum. Modifications to the device/apparatus such as the orientation of the leaflet immobilization supports would allow introduction through a peripheral artery and retrograde from the aorta into the left ventricle and then the left atrium.

In another method aspect, magnetic resonance imaging, fluoroscopy, and different forms of echocardiography, including transesophageal echocardiography including transesophageal echocardiography, transthoracic echocardiography, intracardiac echocardiography, and three-dimensional cardiography may assist with device position and advancement within the heart and body, leaflet immobilization, and the determination if the leaflet apposition achieved by the device is adequate.

In another method aspect, the device may be used for tricuspid valve repair, by gaining access to the right atrium through a direct incision or through a percutaneous route and by advancing the device through the right ventricular outflow tract and into the pulmonary artery to establish proper orientation with respect to the individual tricuspid valve leaflets.

BRIEF DESCRIPTION OF THE DRAWINGS

FIG. 3A is a schematic representation of a human heart and one embodiment of a catheter having an elongate body, an anchor zone, and tissue manipulators showing the position within the heart and blood vessels that provides correct orientation.

FIG. 15 is a side view of the coapted anterior and posterior heart leaflets secured together by a fastening material resulting in edge-to-edge apposition, also referred to as a "bow-tie" repair.

DETAILED DESCRIPTION OF THE PREFERRED EMBODIMENT

Figure 1:
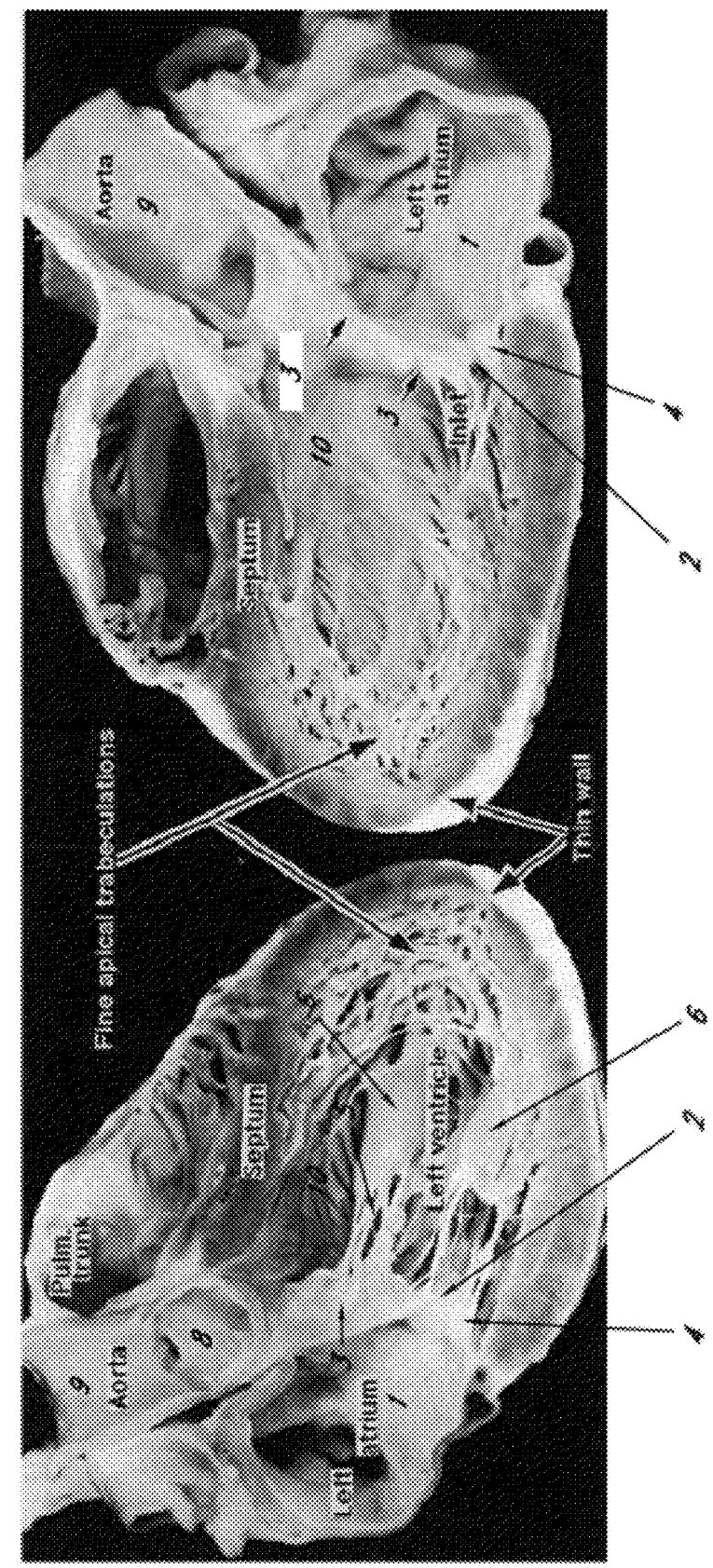
FIG. 1 is a photograph of a pathologic specimen of a human heart sectioned along its long axis, demonstrating the pertinent anatomical structures and landmarks important to device operation.

In FIG. 1, a longitudinal section of the human heart is shown demonstrating the left atrium 1, the mitral valve orifice 2, the anterior leaflet of the mitral valve 3, and the posterior leaflet of the mitral valve 4. The subvalvular apparatus consists of the numerous chordae tendinae 5 and the papillary muscles 6. The left ventricular outflow tract (LVOT) 10 is a channel formed by the anterior leaflet of the mitral valve 3 and the interventricular septum. This Figure demonstrates the pathway the distal end of the device must take from the left atrium 1, through the mitral valve orifice 2, between the papillary muscles 6, through the LVOT 10, across the aortic valve 8 and into the ascending aorta 9.

Figure 2:
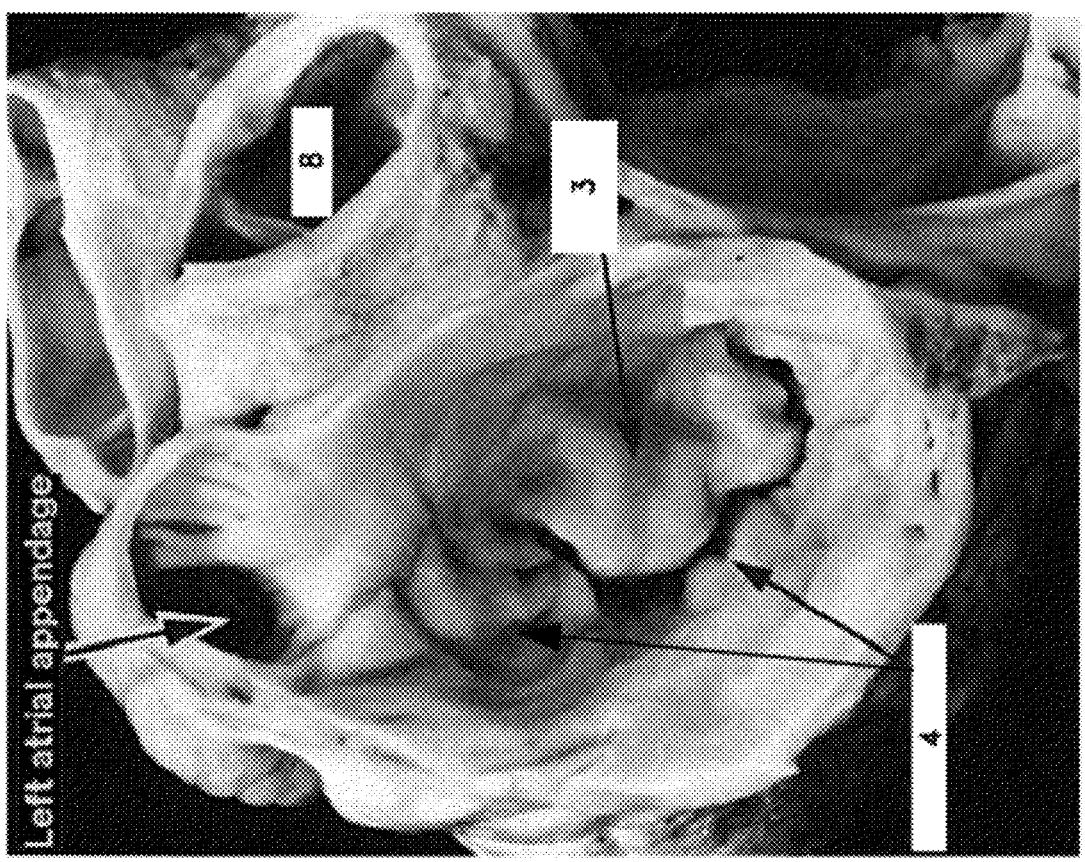
FIG. 2 is a photograph of a pathologic specimen of a human heart, sectioned in short axis at the level of the left atrium, demonstrating the anatomy of the mitral valve leaflets as viewed from the perspective of the left atrium and the approach of the invention.

In FIG. 2, a short axis view of the mitral valve is seen at the level of the left atrium. This demonstrates the asymmetric nature of the mitral valve leaflets. The posterior leaflet 4 has a broad base and of narrow width, while the anterior leaflet 3 has a relatively narrow base and a substantial width.

Figure 3:
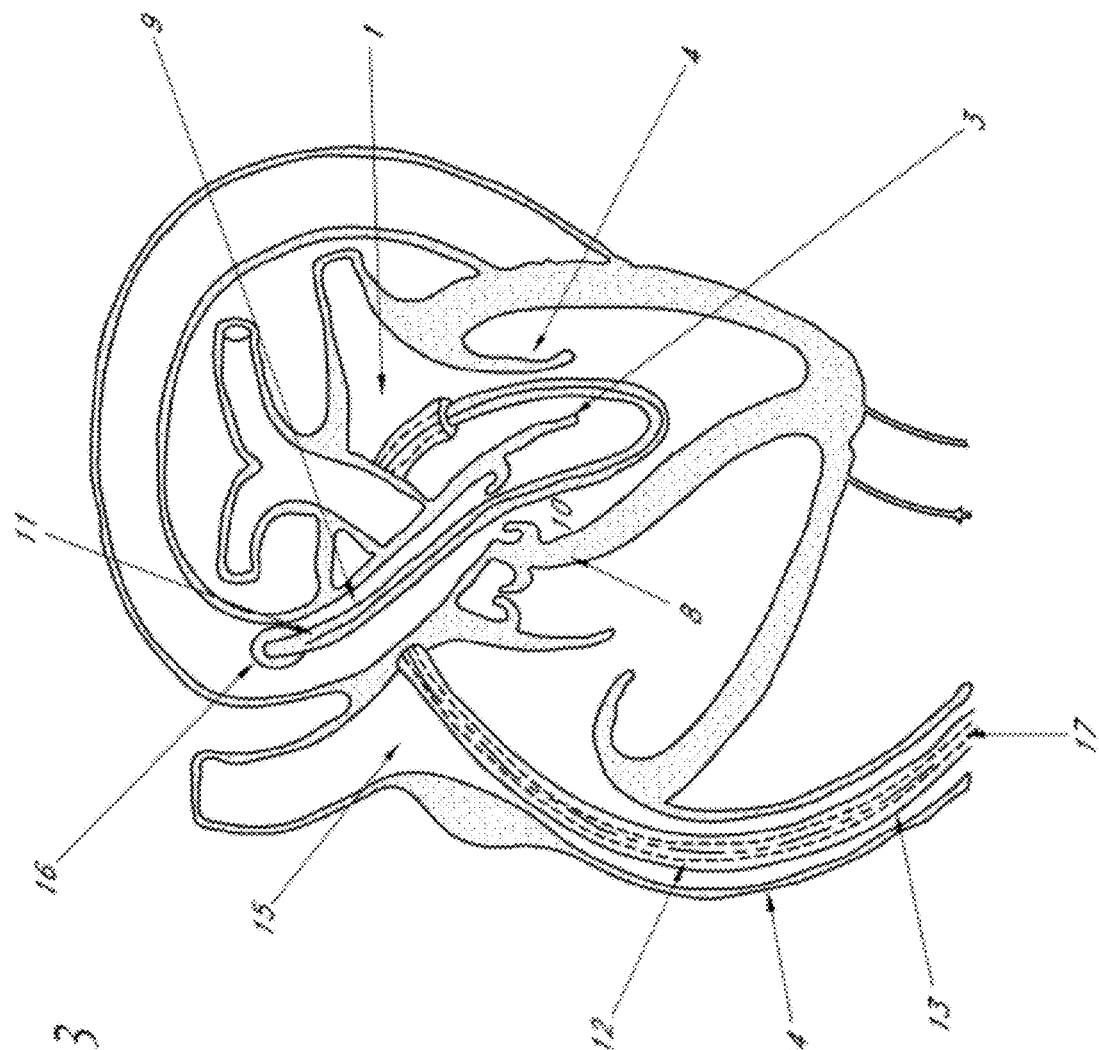
FIG. 3 is a schematic representation of a human heart and one embodiment of the present invention showing the position within the heart and blood vessels that provides correct orientation.

One embodiment of the orientation catheter 11 and a Housing Catheter 18 and the Valve Immobilization Catheter (VIC) 19 in relation to these heart structures is depicted schematically in FIG. 3 and FIG. 3A respectively. The distal end 11 of the catheter is the one advanced through the body; the proximal end 13 is the end closest to the operator. In subsequent Figure, the proximal end is illustrated at the left portion of the Figure, and the distal end at the right, unless stated otherwise. A sheath 12 is placed through a central venous access and advanced through the inferior venae cavae 14, into the right atrium 15, and trans-septally into the left atrium 1 using the conventional cardiac catheterization technique. The catheter 11 is advanced through the sheath into the left atrium 1, between the anterior 3 and posterior 4 leaflets, into the LVOT 10, and through the aortic valve 8 into the ascending aorta 9. This position through the LVOT 10 orients the catheter with respect to the anterior mitral valve leaflet 3 and the posterior leaflet 4.

The preferred embodiment shown in FIG. 3 employs an inflatable balloon to assist the operator in placing a guide wire from the left atrium to ascending aorta. The length of the catheter 11 is sufficient for the length of the approach from the insertion site to the ascending aorta. Balloon and catheter constructions are well known in the art. U.S. Pat. No. 6,051,014 ("the '014 patent"), the contents of which are incorporated by reference in their entirety herein, discloses various balloon-tipped catheter construction. All of the foregoing ranges illustrate typical and preferred dimensions only; one could employ a catheter that is greater or shorter in any of these dimensions. What is important is that the catheter has the dimensions that permit one to insert it via the desired route. The catheter illustrated in FIG. 3, for example, has the dimensions that make it appropriate for percutaneous placement through central venous access such as the right femoral vein.

The inflated balloon 16 at the distal end of the catheter 11 is filled with a gaseous substance such as air, or $CO_2$. The gaseous substance gives buoyancy to the inflated balloon 16 and permits floatation in liquid substances such as blood. With the distal end of the catheter 11 attached to the inflated balloon 16 the flow of blood naturally carries the catheter 11 through the valve leaflets 3,4; around and into the LVOT 10, and up through the aortic valve 8 into the ascending aorta 9. In an alternative embodiment, the entire device may be incorporated into one or more balloon-tipped catheters.

Once the orientation catheter 11 is in place, a guide wire 17 may then be advanced through the lumen of the catheter 11, the guide wire acting as a path to withdraw or advance catheters or apparatuses easily to the ascending aorta 9. In another embodiment, one could advance this catheter with or without a balloon tip over a guide wire into its position in the aortic root using techniques known to those skilled in the art. At this point, the catheter 11 may be withdrawn and the guide wire 17 left in place. Alternatively, the catheter 11 and the guide wire 17 may both be left in their same position. In either case, the orientation catheter 11 and/or the guide wire 17 may serve as a path to advance and place the device Housing Catheter 18 and the Valve Immobilization Catheter (VIC) 19.

The following embodiments generally refer to FIGS. 4 through 15. In one embodiment, the orientation catheter once in place in the ascending aorta may be removed over a guide wire and the device Housing Catheter 18 advanced over the wire until its distal end is in the ascending aorta. See FIG. 3A. The device Housing Catheter 18, like the orientation catheter 11, is made of material flexible and torqueable, preferably of a polymeric material but any other biocompatible material may be used. The device Housing Catheter 18 contains a central lumen through which the valve immobilization catheter (VIC) 19 can be advanced, and has in its wall holes 20, 21 (herein referred to as "portals") that, once the Housing Catheter 18 is in place in the ascending aorta with the assistance of the orientation catheter, are specifically aligned with the locations of the anterior 3 and posterior 4 leaflets to allow for the deployment of leaflet immobilization supports (LISs) 22, 23 incorporated into the VIC 19 that unfold and project out of the apparatus to immobilize the individual leaflets. The Housing Catheter 18 also contains holes within its walls for the extension of fixation devices 24 and 25 from the VIC 19. A distal end D of the housing catheter 18 can include an anchor zone AZ, as discussed below. The VIC 19 is a catheter with a central lumen for a guide wire, is made of material flexible and torqueable, and has a semi-rigid portion that contains the leaflet immobilization apparatus, which consists of the leaflet immobilization supports 22, 23, the spring hinge 26, and the fixation devices 24, 25. In an alternative embodiment, the fixation devices 24, 25 may be incorporated into another element of the catheter system such as the Housing Catheter 18, or in a separate portion of the VIC 19 at a distance from the other parts of the leaflet immobilization apparatus. In an alternative embodiment, the device Housing Catheter 18 and VIC 19 may be incorporated into a single catheter with a movable core and may contain a central lumen for a guide wire.

Monitoring the advancement and manipulation of the orientation catheter 11, the guide wire 17, the device Housing Catheter 18, and the VIC 19 may be done by a variety of visualization techniques including, but not limited to MRI, fluoroscopy, endoscopy, thoracoscopy, transthoracic, intracardiac, and transesophageal echocardiography. These and other visualization techniques are employed throughout the present invention to track the movement of the apparatus inside a human body.

Figure 4:
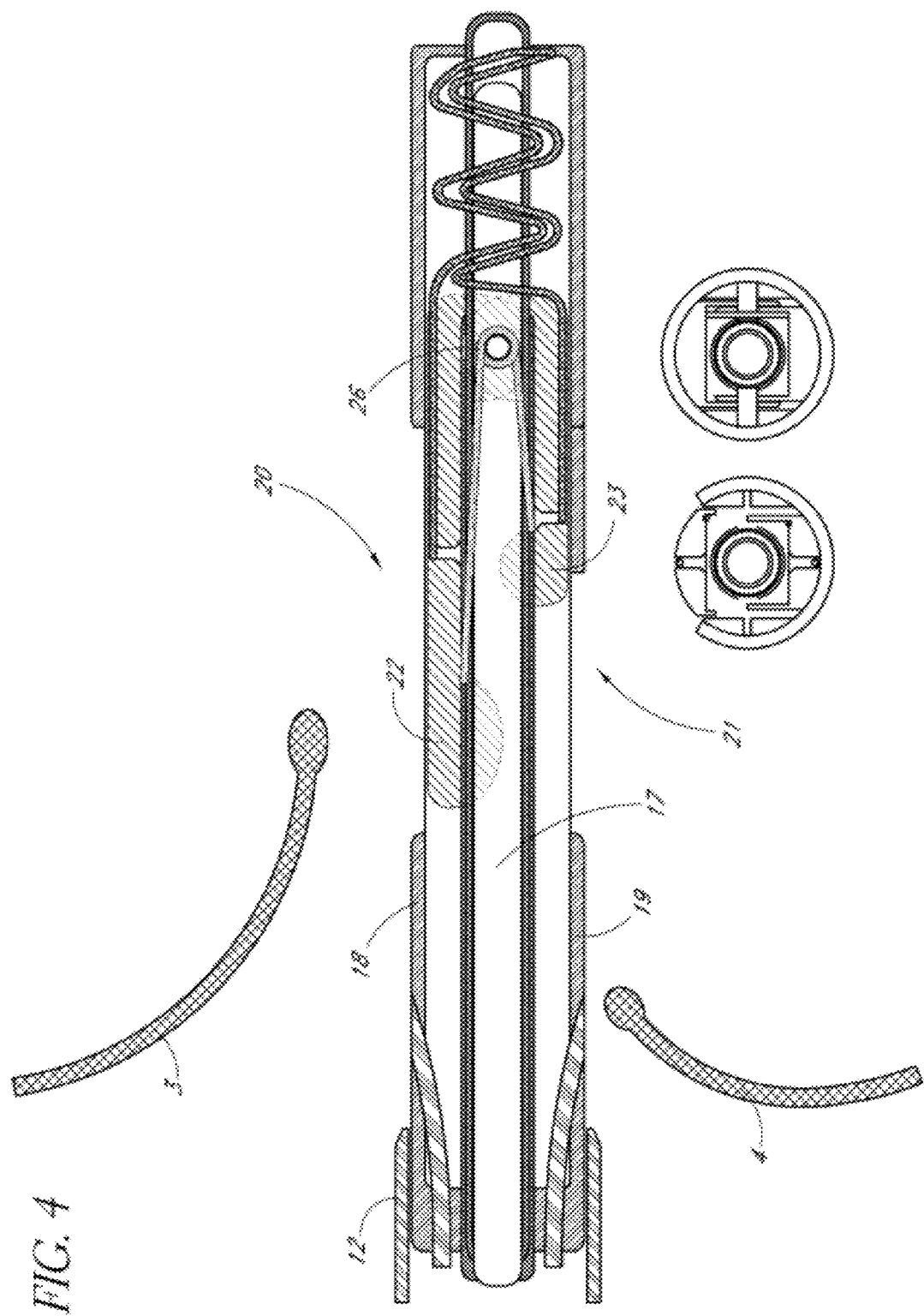
FIG. 4 is a side view of one embodiment of the present invention showing the device positioned between the two heart valve leaflets prior to leaflet immobilization support deployment.

FIG. 4 depicts in longitudinal section one embodiment of the present invention for mitral heart valve repair showing a Housing Catheter 18, advanced through a sheath 12 placed as depicted in FIG. 3, over a guide wire and into the proper position between the mitral valve leaflets 3 and 4. The VIC 19 with its incorporated leaflet immobilization apparatus consisting of the leaflet immobilization supports 22, 23, and spring hinge 26 has been advanced over a guide wire through the device Housing Catheter 18 and into proper position with respect to the mitral valve leaflets 3 and 4. Through advancement, retraction, and torquing of the VIC 19 by the operator, the VIC allows the operator to manipulate the incorporated leaflet immobilization apparatus. The function of the leaflet immobilization apparatus (consisting of the leaflet immobilization supports 22, 23, spring hinge 26, and fixation devices 24, 25) is to isolate, immobilize, and fixate the individual valve leaflets. These components of the leaflet immobilization apparatus are preferably made of a sterile, biocompatible material such as metal or plastic. The leaflet immobilization apparatus is preferably cylindrical in shape, but may also be rectangular, conical or a multitude of other shapes. The leaflet immobilization apparatus comprises two leaflet immobilization supports ("LIS")—one anterior 22 and one posterior 23 connected to a spring hinge 26 incorporated into the VIC 19. In mitral heart valve repair, the anterior LIS 22 may be longer than the posterior LIS 23, thus taking into account the anatomical difference in the size and shape of an anterior mitral valve leaflet 3 compared to a posterior mitral valve leaflet 4 as demonstrated in FIG. 2. By way of example, the shape of the LIS 22, 23 may resemble thin rectangular arms or wings that are connected by a hinge 26. However, the design of the LIS 22, 23 may be shaped in a variety of different forms. For example, the LIS 22, 23 may be circular, triangular, square, oval, or elliptical. The LIS 22, 23 may also be straight or curved. Differences in the sizes of the LIS 22 and 23 may be tailored to the anatomical requirements of a particular surgical repair and patient. In any case, the shape of the LIS 22, 23 are designed to fit within the lumen of a catheter and, when deployed, to optimally interface with the unique anatomical shape of the anterior leaflet 3 and posterior leaflet 4, respectively. In addition, the hinge connecting the LIS 22, 23 may also comprise a spring 26. When the LIS 22, 23 are located outside the lumen of the catheter, the spring hinge 26 connecting the LIS 22, 23 extends the LIS 22, 23 outward and away from catheter system. The spring hinge 26 limits the range of movement of the LIS 22, 23 from a closed position, or zero degrees, to an open position not to exceed 90 degrees away from the catheter system. The spring 26 exerts relatively little force against the LIS 22, 23 in the open position. When the LIS 22, 23 is contained within the lumen of the Housing Catheter 18, the walls of the lumen force the LIS 22, 23 inward. In an alternative embodiment, the closed position of LIS 22, 23 may be maintained by a latch mechanism that can be released by an actuator in the proximal portion of the VIC 19. Thus, in the lumen of the housing catheter, the LIS 22, 23 are flush within the Housing Catheter 18, and the spring hinge 26 is loaded with the force of the LIS 22, 23 in a closed position. To ease advancement of the VIC with its incorporated leaflet immobilization apparatus, the Housing Catheter 18 may contain grooves shaped to receive the LIS 22, 23, or to receive the VIC 19 in a proper orientation so that LIS 22, 23 are directed properly toward the exit ports 20, 21 in the Housing Catheter 18. In an alternative embodiment, the Housing Catheter 18 and the VIC 19 with its incorporated leaflet immobilization apparatus may be incorporated into a single catheter with a moveable core that allows for the manipulation of the LIS 22,23, the spring hinge 26, and fixation devices 24, 25 by actuator or actuators at the proximal end of the catheter system, or by direct manipulation of the core itself at the proximal end of the catheter system.

FIG. 4 thus depicts the VIC 19 advanced within the Housing Catheter 18 and the LIS 22, 23 in closed positions. The VIC 19 has been advanced within the Housing Catheter 18 so that the LIS 22, 23 are positioned below the ventricular aspect of the open anterior 3 and posterior 4 leaflets. The LIS 22, 23 are now ready for deployment.

Figure 5:
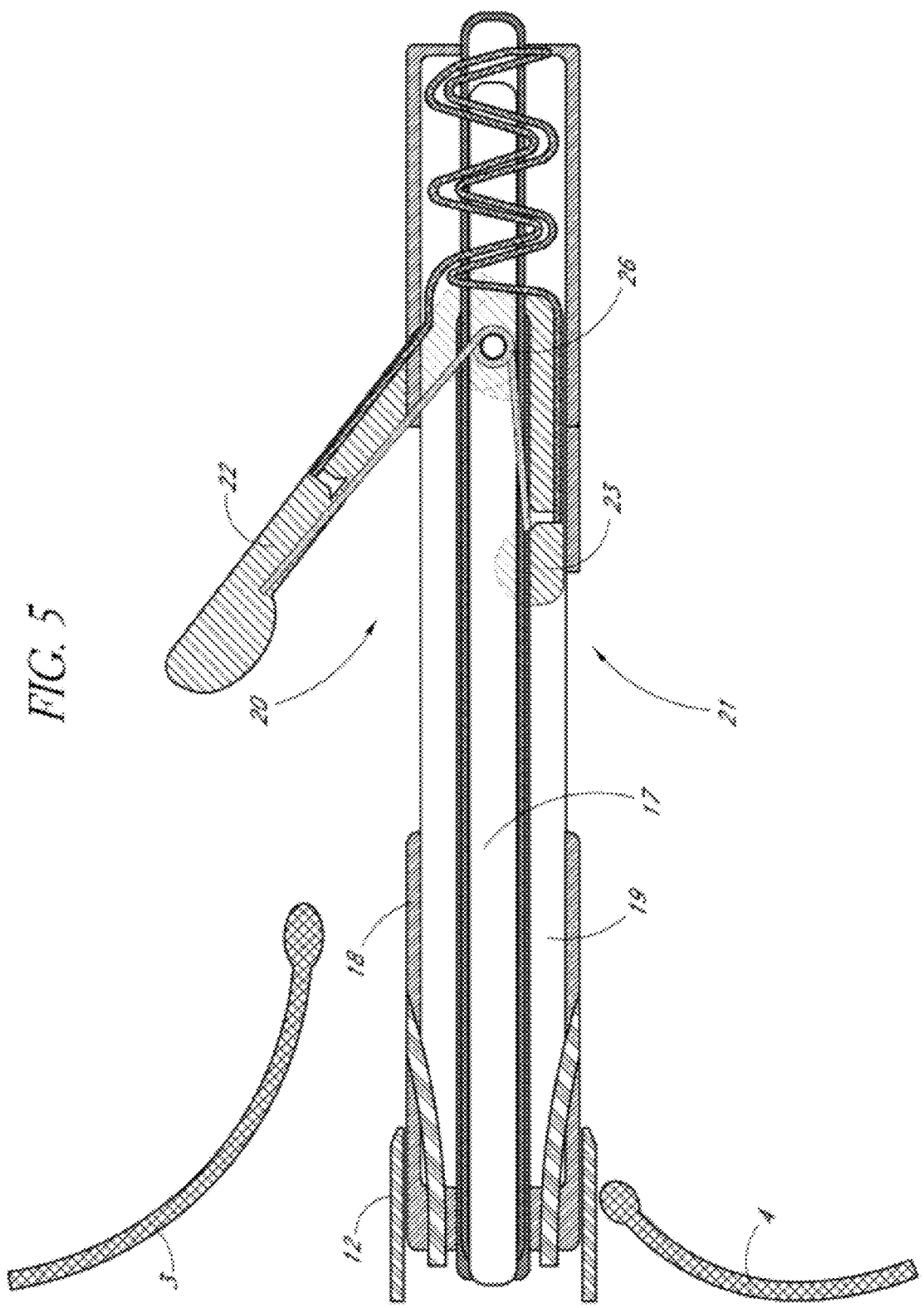
FIG. 5 is a side view of one embodiment of the present invention showing the anterior leaflet immobilization support partially extended from an anterior portal and positioned below the anterior leaflet.
Figure 6:
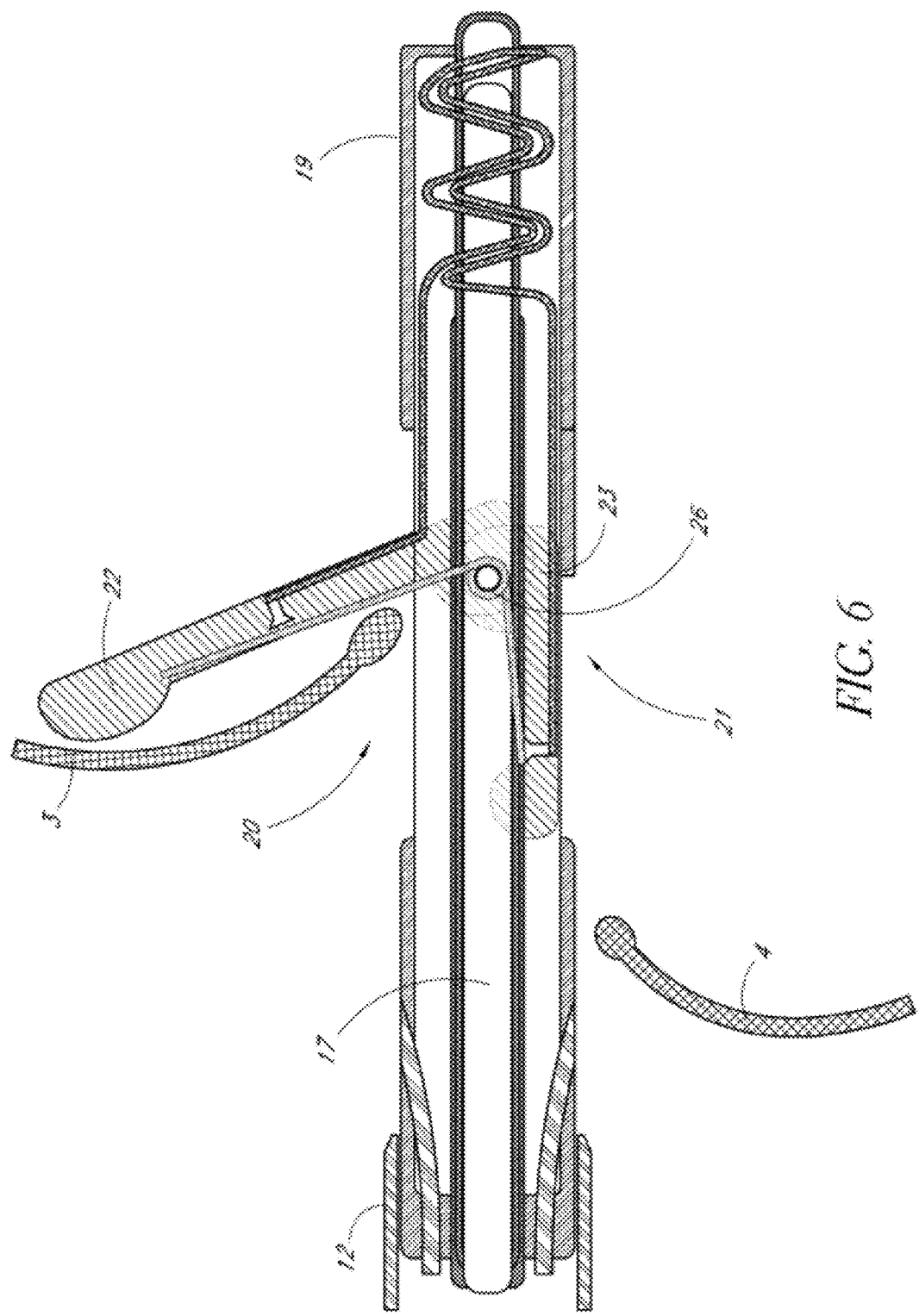
FIG. 6 is a side view of one embodiment of the present invention showing the anterior leaflet immobilization support fully extended and engaging the anterior leaflet.

FIGS. 4, 5 and 6 sequentially depict one embodiment of the present invention's independent deployment of anterior LIS 22. In FIG. 4 the VIC 19 is shown advanced toward the distal end of the housing catheter 18 that has an anterior portal 20. The proximal end of VIC 19 may extend outside the proximal end of the housing catheter 18. This enables the operator to push and pull the VIC 19 in a distal or proximal direction within the catheter. As the operator pulls it in the proximal direction, the leaflet immobilization apparatus (consisting of the LIS 22,23, and the hinge 26) moves in a proximal direction within the Housing Catheter 18. In addition, gradually, the anterior LIS 22 independently extends outward from the anterior portal 20 as the entire length of the anterior LIS 22 moves proximally toward the open space of the Housing Catheter's 18 anterior portal 20. The anterior LIS 22 independently extends outward first because of the differential lengths of anterior LIS 22 and posterior LIS 23 and because of the differential locations of the anterior portal 20 and the posterior portal 21. Without the containment of the lumen walls of the Housing Catheter 18, the force of the loaded spring hinge 26 extends the anterior LIS 22 through the anterior portal 20 of the Housing Catheter 18 away from the VIC 19. In an alternative embodiment of the present invention, an operator may release the anterior LIS 22 or actuate the deployment of the anterior LIS 22 by way of an actuator located at the proximal end of the VIC 19. Referring back to FIG. 1, the tips of the mitral valve leaflets 3 and 4 point in a ventricular direction when open. Thus, the angle of the deployed anterior LIS 22 allows for the engagement of the ventricularly directed anterior valve leaflet 3. Incorporating FIG. 1's frame of reference regarding the mitral valve leaflets 3 and 4, FIG. 5 shows the anterior LIS 22 free from the lumen of the housing catheter 23 and in a partially extended position below the anterior mitral valve leaflet 3. FIG. 6 next shows the anterior LIS 22 in a fully extended position below the anterior leaflet 3, and engaging the anterior leaflet 3. Once the anterior LIS 22 is fully extended and positioned below the anterior leaflet 3, the flexible and torqueable nature of the housing catheter 18 and the VIC 19 allow the operator to move and adjust the housing catheter/VIC system until he or she has determined that the anterior LIS 22 is positioned optimally below the anterior leaflet 3, using imaging techniques such as fluoroscopy, MRI, transesophageal, intracardiac, transthoracic, or three-dimensional echocardiography as needed.

Figure 7:
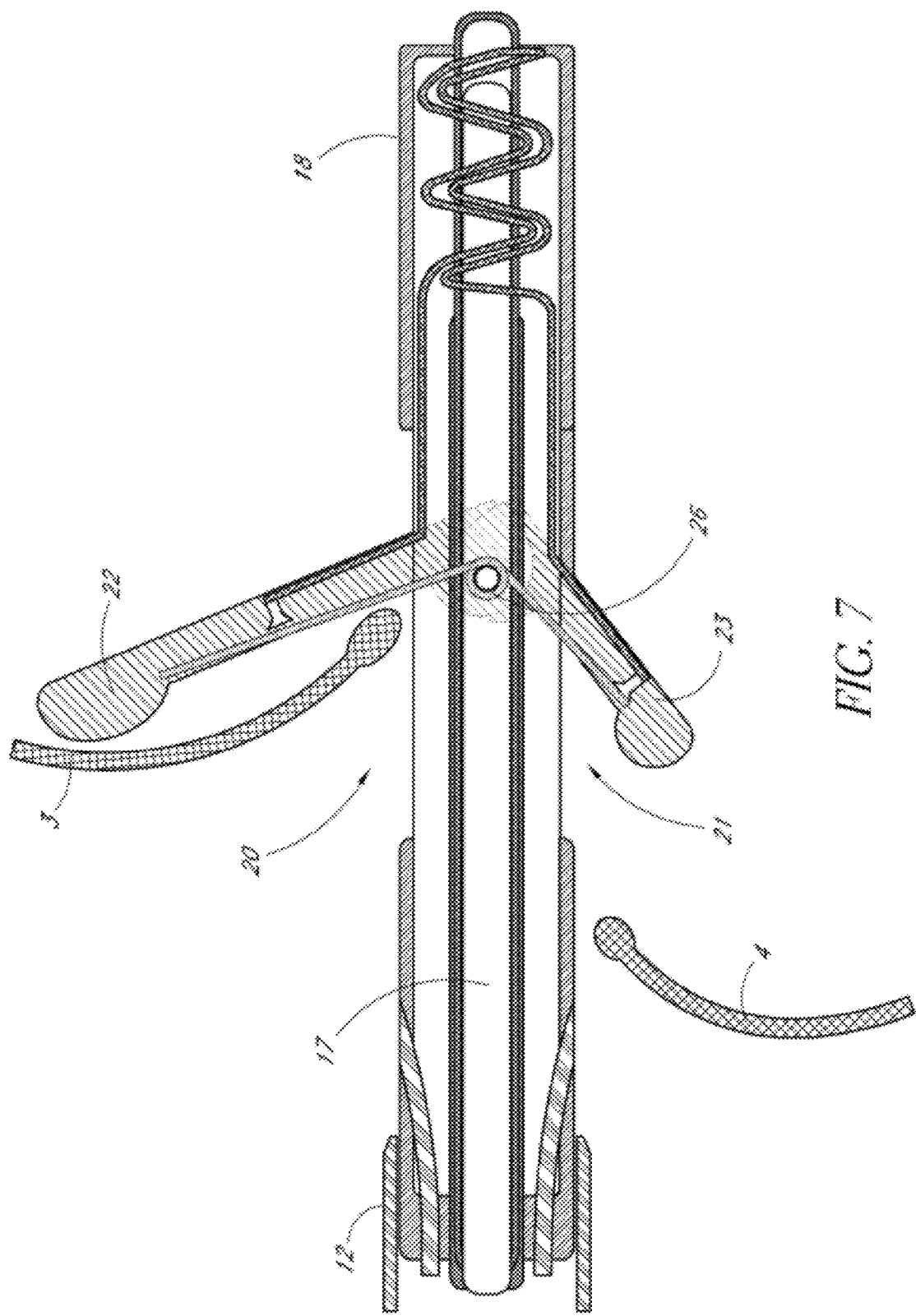
FIG. 7 is a side view of one embodiment of the present invention showing the anterior leaflet immobilization support fully extended and in contact with an anterior heart valve leaflet, and the posterior leaflet immobilization support partially extended from a posterior portal and positioned below the posterior leaflet.
Figure 8:
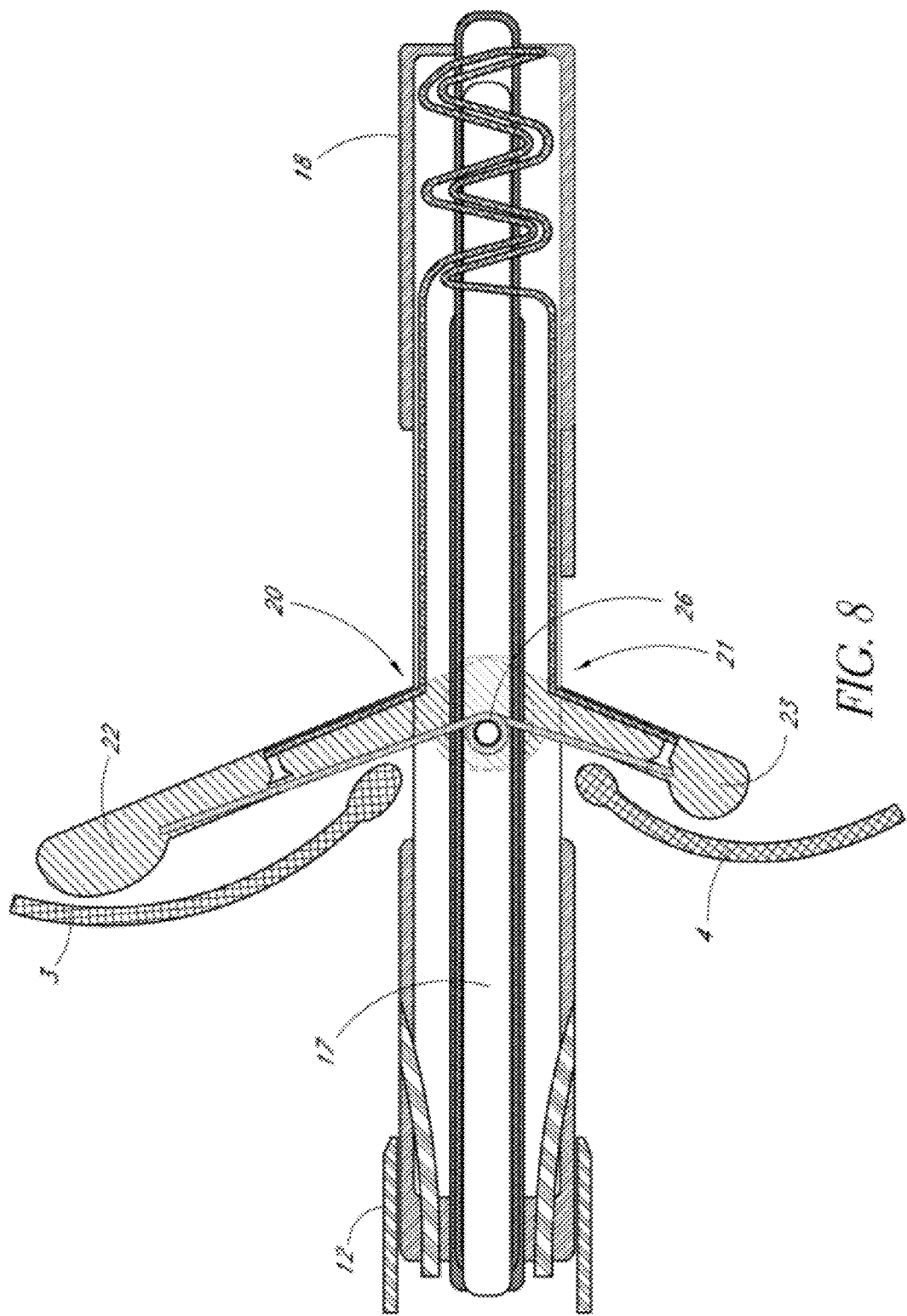
FIG. 8 is a side view of one embodiment of the present invention showing the anterior leaflet immobilization support fully extended and engaging the anterior heart valve leaflet, and the posterior immobilization support fully extended and engaging the posterior leaflet.
Figure 9:
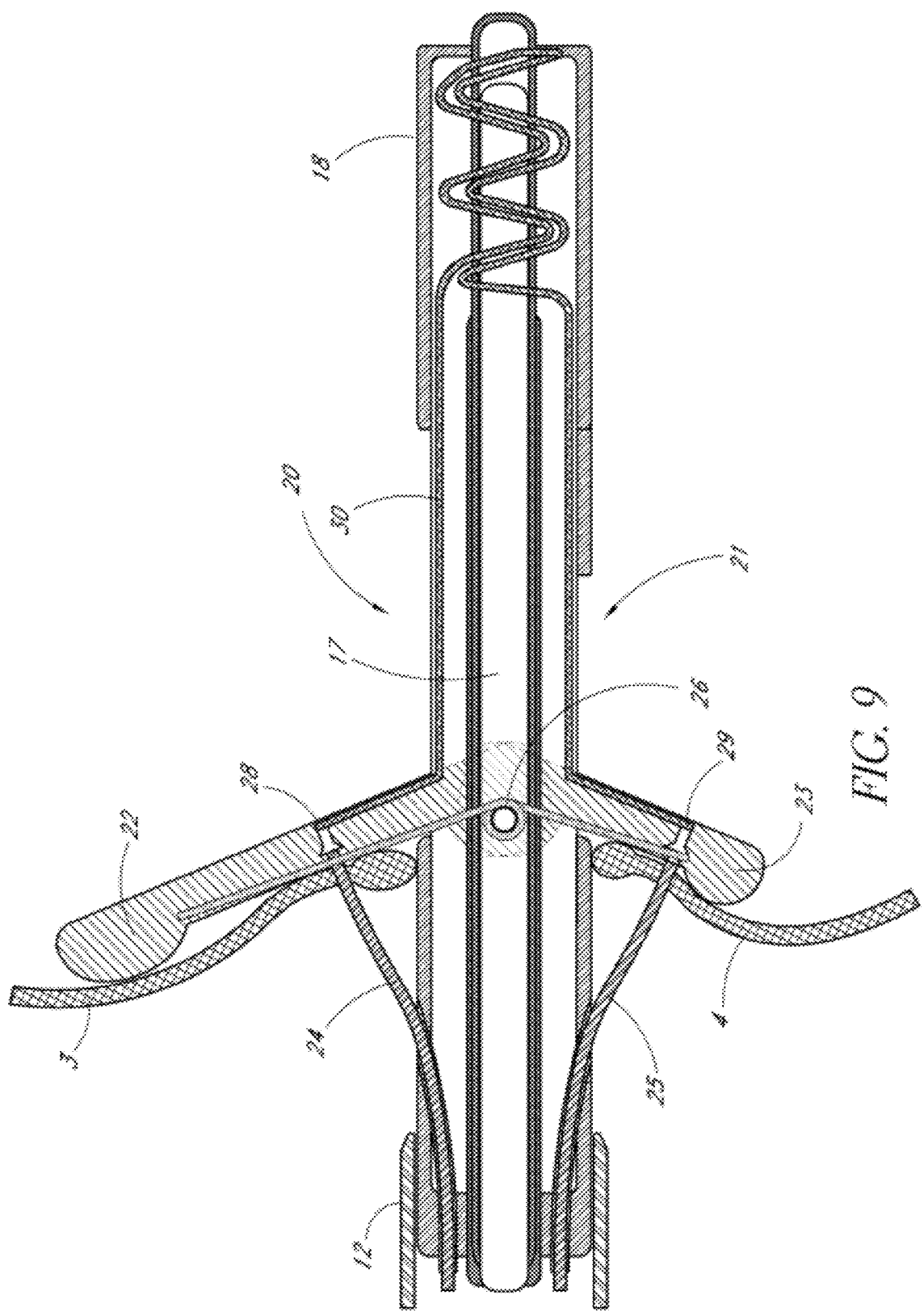
FIG. 9 is a side view of one embodiment of the present invention showing the leaflet immobilization supports engaging the anterior and posterior leaflets with the fixation devices deployed and securing the anterior and a posterior leaflets.

FIGS. 7 and 8 sequentially depict one embodiment of the present invention showing the independent deployment of posterior LIS 23. Once the anterior LIS 22 extends through the anterior portal 20, the operator may further pull VIC 19 in a proximal direction. This movement will cause the posterior LIS 23 to move from the lumen of the catheter to the opening of the posterior portal 21. The posterior LIS 23 may be shorter than the anterior LIS 22 taking into account the size difference of the anterior 3 and posterior 4 mitral valve leaflets. Similar to the independent deployment of anterior LIS 22, posterior LIS 23 gradually and independently springs to an open position as the operator pulls the VIC 19 proximally. In an alternative embodiment of the present invention, an operator may actuate the release and/or deployment of the posterior LIS 23 by way of an actuator located at the proximal end of the VIC 19. In FIG. 7, the posterior LIS 23 is shown in a partially extended position shortly after clearing the lumen of the Housing Catheter 18 through the posterior portal 21. Similar to anterior LIS 22 positioning, the posterior LIS 23 is positioned at the ventricular side of posterior leaflet 4. In FIG. 8, posterior LIS 23 is in a fully deployed position and is optimally positioned under posterior leaflet 4. Upon determining the optimal positioning of the LIS 22, 23 in relation to the anterior 3 and posterior 4 leaflets, fixation devices 24, 25 are used to immobilize the leaflets 3, 4 in one embodiment of the invention as depicted in FIG. 9. The fixation devices 24, 25 are preferably curved needles, made of plastic or metal, that, upon manipulation by an operator of an actuator at the proximal end of the device, extend from the proximal end of the VIC 19 in relation to the LIS 22, 23. However, other fixating devices and methods are contemplated as well. Importantly, the specific angles of the fixation devices extensions in relation to LIS 22,23 allow for the fixation of the leaflets in their central portions, which prevents leaflet tearing and ensures the optimal amount of leaflet tissue is encaptured, improving the surgical result. If, using visual aids such as fluoroscopy, transesophageal, transthoracic, and/or intracardiac echocardiography, the operator determines that the leaflets 3, 4 are not in optimal apposition for a successful repair, the fixating devices 24, 25 may be withdrawn from the leaflets 3, 4 by actuation of the actuator; the leaflet immobilization apparatus is repositioned in relation to the leaflets 3, 4; and the fixating devices 24, 25 are deployed again to pin the leaflets 3, 4. The readjustment of the Housing Catheter 18, the VIC 19, and its leaflet immobilization supports 22, 23 and fixation devices 24, 25 may be repeated until the optimal apposition of the leaflets 3, 4 is achieved. After an operator determines that both leaflets 3, 4 are pinned in an optimal position the operator may lock the position of the fixation devices 24, 25 through further actuation of the fixation devices 24, 25.

Figure 10:
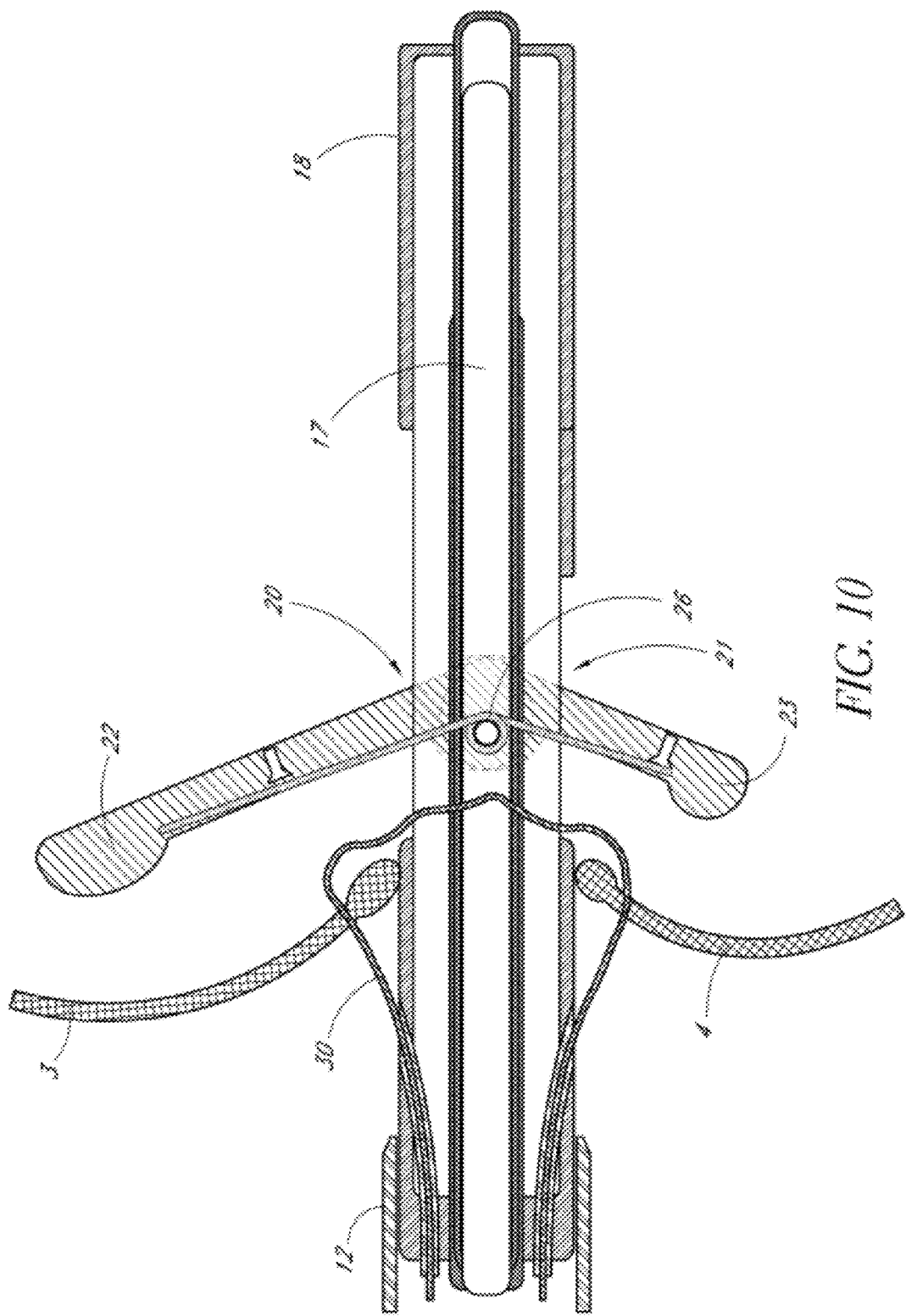
FIG. 10 is a side view of one embodiment of the present invention showing the fully extended leaflet immobilization supports disengaging the anterior and posterior leaflets, and fastening material drawn through the these leaflets.

FIG. 9 also depicts one embodiment of the present invention in which a fastening material is prepared to be drawn through the edges of the anterior 3 and posterior 4 mitral valve leaflets. In one embodiment of the present invention, anterior 22 and posterior 23 LIS may each hold a link 28, 29. Each link 28, 29 is connected to one end of a continuous fastener material 30. In an alternative embodiment of the present invention, each end of the fastener material 30 may be attached to some other needle capturing device. Each link 28, 29 receives the piercing point of the fixation devices 24, 25. Subsequent manipulation of an actuator on the proximal end of the catheter by the operator results in the retraction of the fixating devices 24,25 as shown in FIG. 10. The fixating devices 24, 25 return to their original position within Housing Catheter 18 and in the process pull the links 28, 29 and attached fastening material 30 through the leaflets 3, 4. Further withdrawal of the fixating devices 24, 25 proximally by direct manipulation by the operator of the proximal end of the device or by using an actuator at the proximal end of the device results in the tightening of the fastening material 30 through the leaflets 3, 4.

Figure 11:
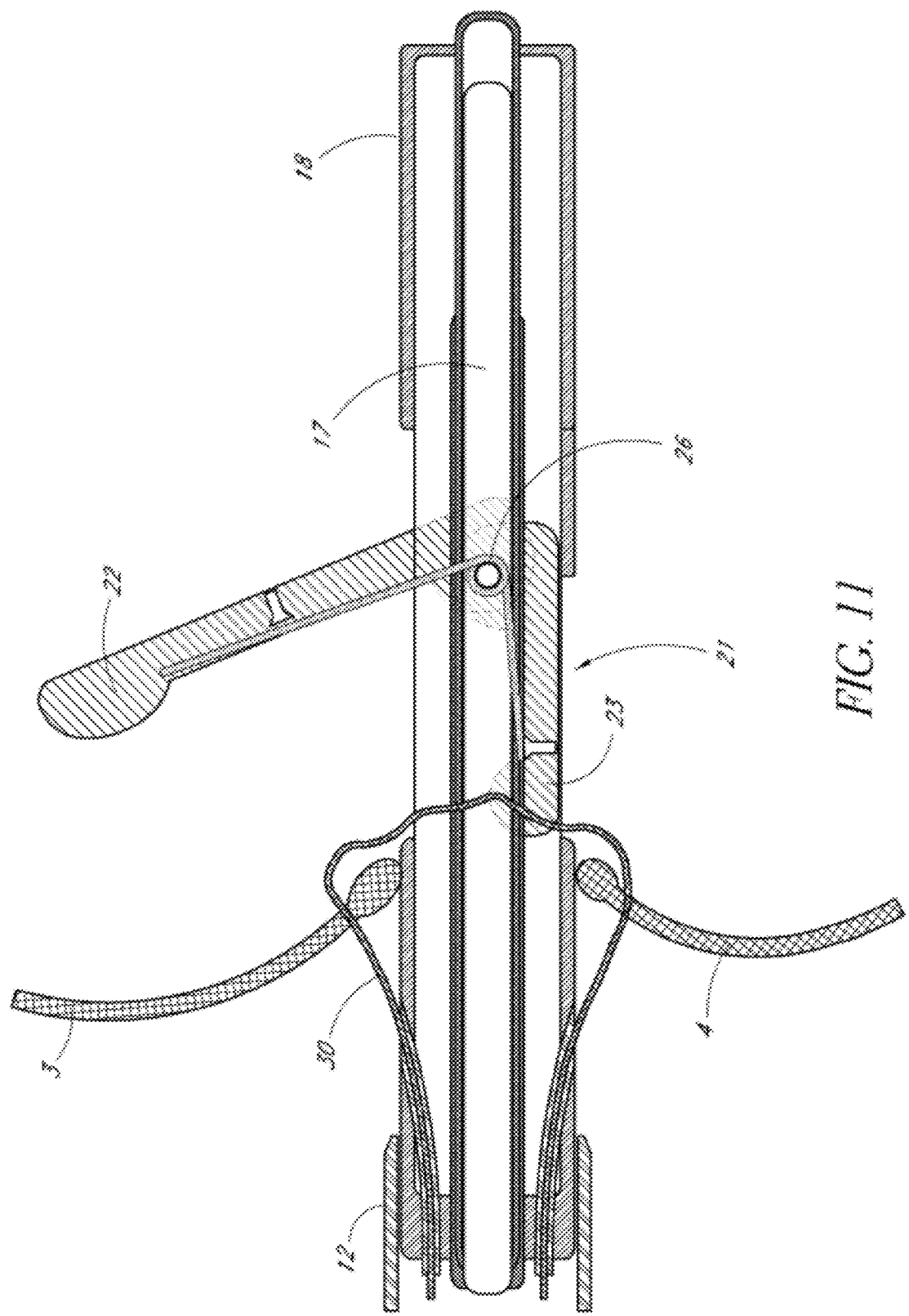
FIG. 11 is a side view of one embodiment of the present invention the anterior leaflet immobilization support extended, the posterior leaflet immobilization support fully withdrawn, and fastening material drawn through the anterior and posterior leaflets.
Figure 12:
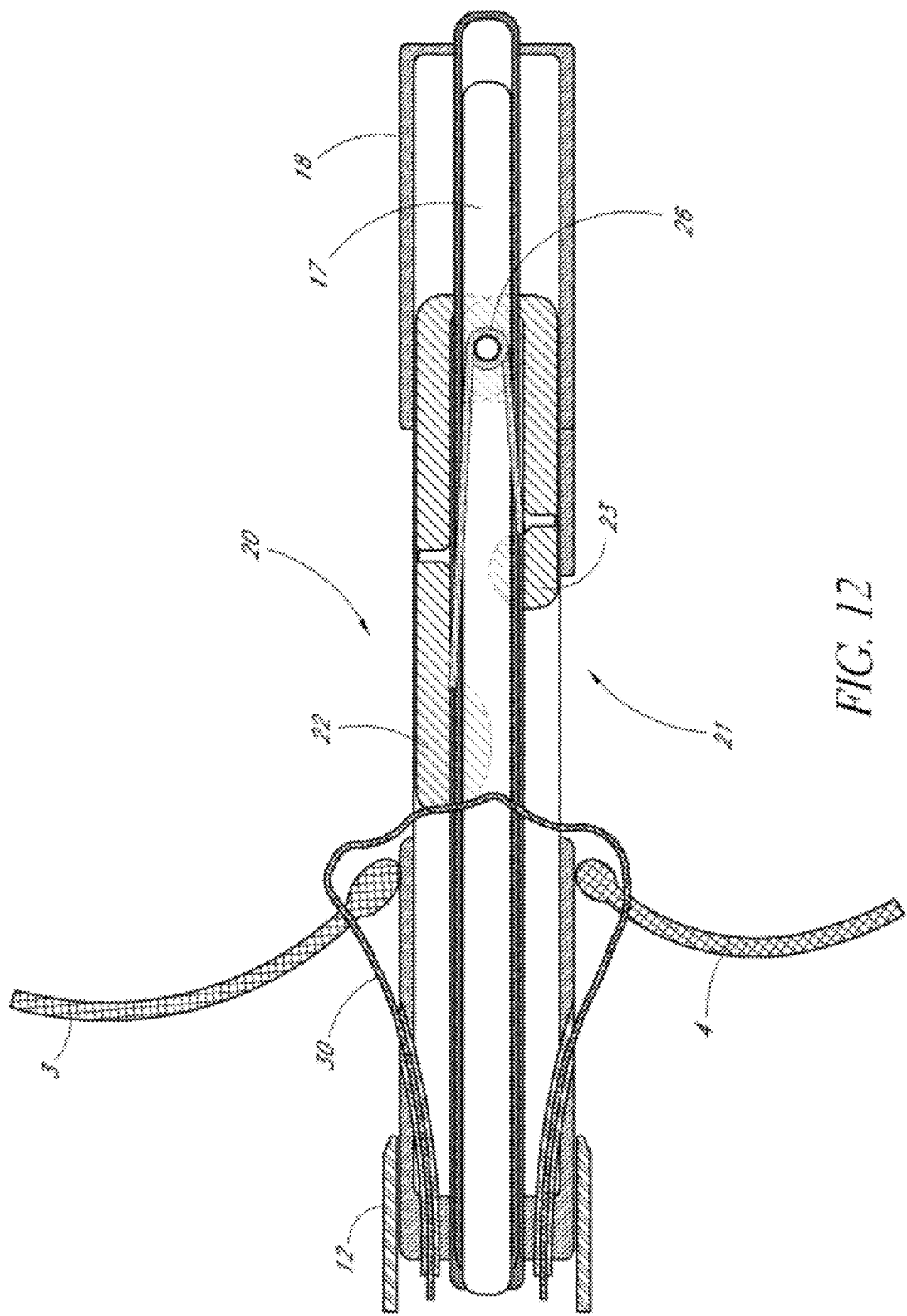
FIG. 12 is a side view of one embodiment of the present invention showing the leaflet immobilization supports completely withdrawn, and fastening material drawn through the anterior and posterior leaflets.

In one embodiment of the present invention, after the fastening material 30 is drawn through the anterior 3 and posterior 4 leaflets, the posterior LIS 23 independently retracts through the posterior portal 21 to its original position flush within the Housing Catheter 18 as shown in FIG. 11. The independent retraction of the posterior LIS 23 may be caused by the distal advancement of the VIC 19 back to its original starting position prior to deployment, or by the manipulation by the operator of an actuator at the proximal end of the device. The spring hinge 26 gives flexibility to and allows for the posterior LIS 23 to return to its position flush within the housing catheter lumen. Further distal advancement of the VIC 19 repeats the same retraction process for the anterior LIS 22 as for the posterior LIS 23 as shown in FIG. 12. In FIG. 12, one embodiment of the present invention depicts both the anterior 22 and posterior 23 LIS in a closed position and advanced past their respective portals 20, 21. In an alternative embodiment of the present invention, the operator may actuate an actuator on the proximal end of the device to independently retract the anterior 22 and posterior 23 LIS, resulting in the same depiction as shown in FIG. 12.

Figure 13:
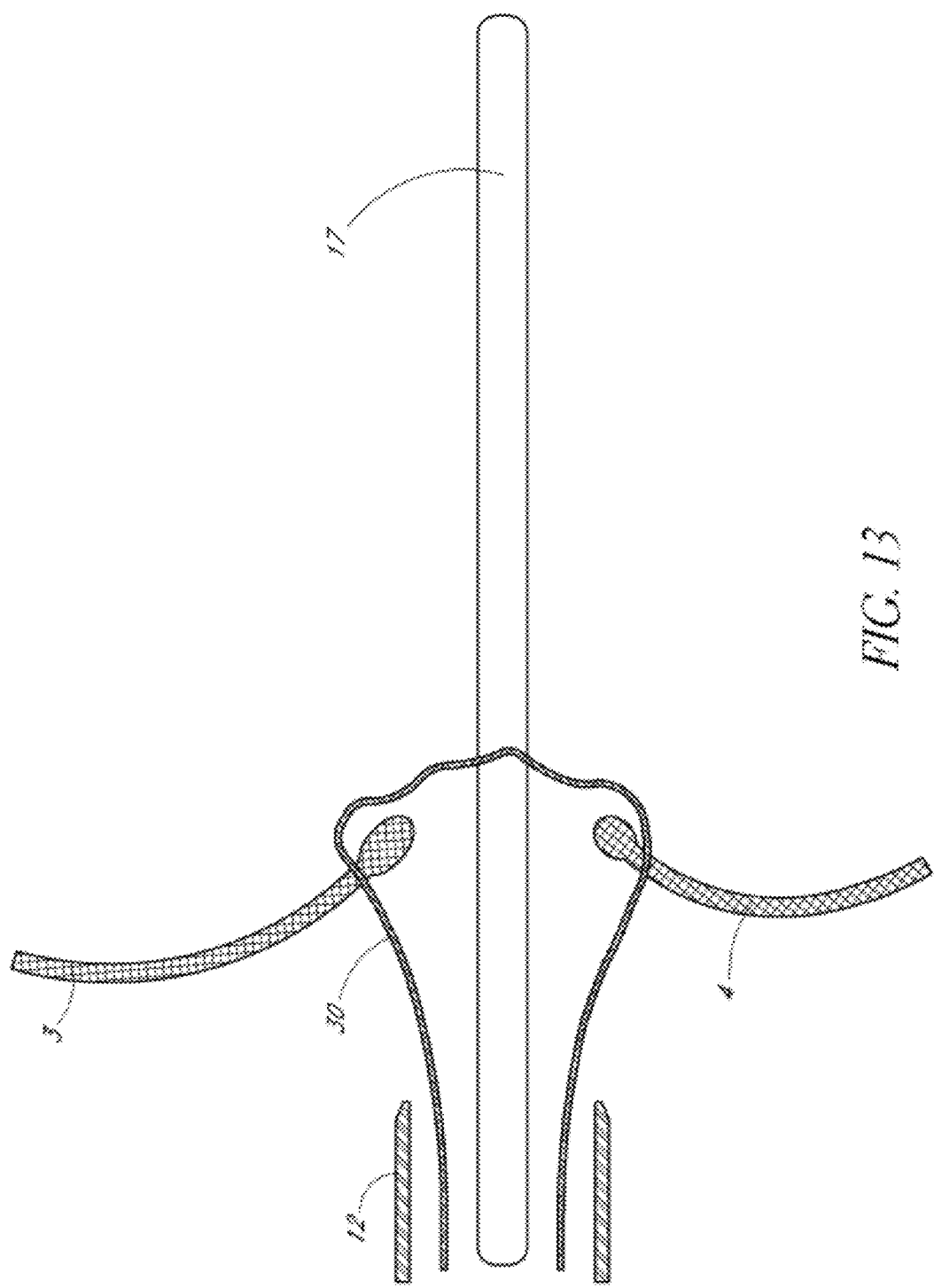
FIG. 13 is a side view of one embodiment of the present invention showing fastening material drawn through the anterior and posterior valve leaflets, with the leaflet immobilization apparatus and its housing catheter withdrawn over a guide wire.
Figure 14:
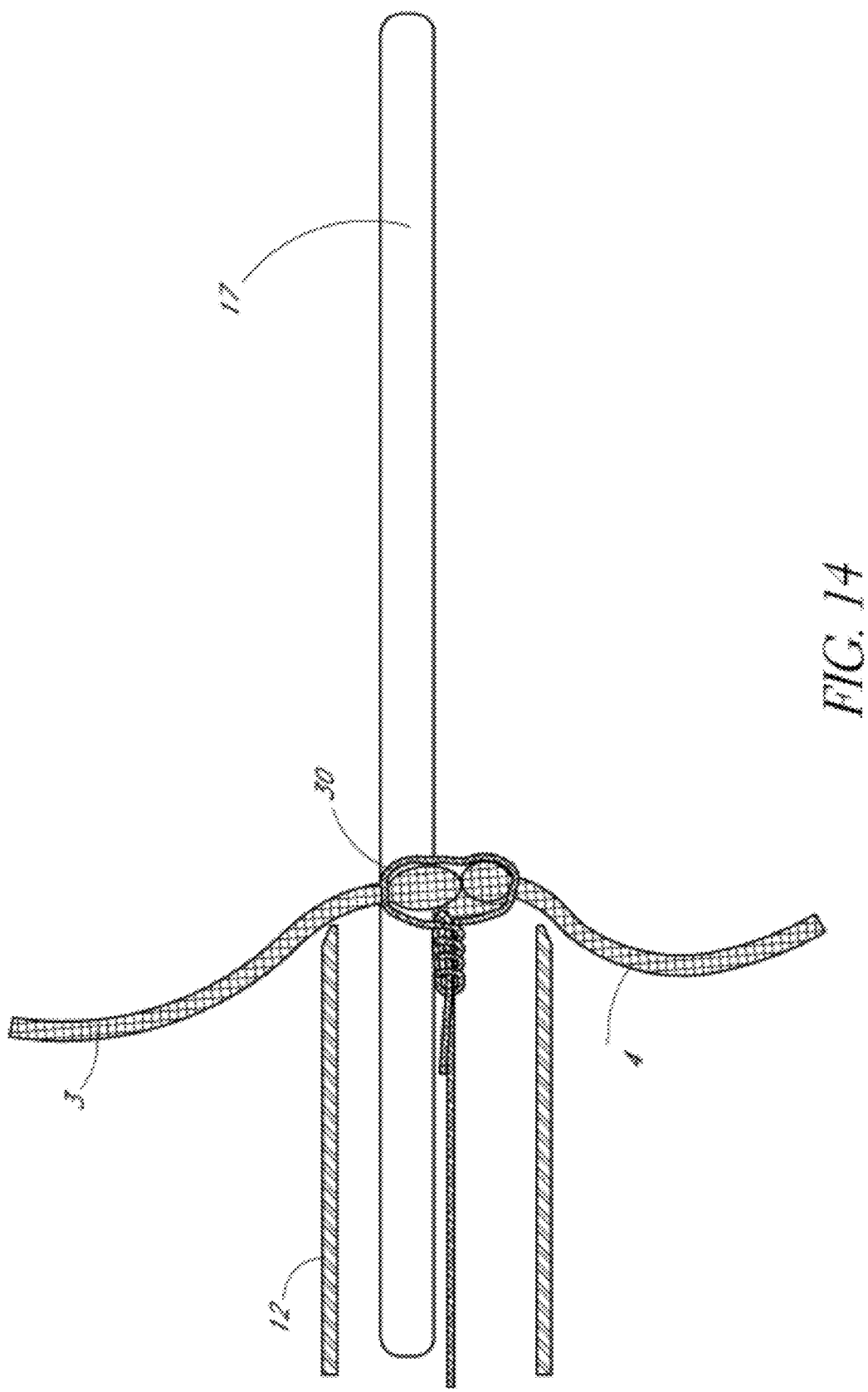
FIG. 14 Shows tying of suture.

In one embodiment of the present invention, the fastening material is released from the arms of LIS 22, 23, and the VIC 19 and the Housing Catheter 18 are then withdrawn together from between the anterior 3 and posterior 4 leaflets over the guide wire 17 as depicted in FIG. 13. The ends of the fastening material 30 are tied together and the knot advanced to the leaflet tissue as shown in FIG. 14. In an alternative embodiment of the present invention, a clip, crimp, or other material may be advanced to tie the fastening material 30 together. The tying of sutures and fastening material is well known in the art and any appropriate method may be employed. In another embodiment of the present invention, the fastening material 30 may act as a crimp, which, after withdrawal of the VIC 19 and Housing Catheter 18, is sealed and released remotely be the operator.

Upon completion of the bow-tie repair, the guide wire 17 is removed from between the leaflets 3, 4 as shown in FIG. 15.

Although certain specific methods and devices have been described herein, the inventors contemplate the invention as more generally directed to methods of orienting catheters in the heart, and performing procedures within the heart, as well as more generally to catheters for enabling such procedures. For example, one aspect of the invention comprises a method of performing a procedure in the heart. The method comprises the steps of providing a catheter, having an elongate flexible body. The body comprises a proximal end, a distal end, and procedure zone, spaced proximally apart from the distal end. As will be apparent to those of skill in the art in view of the disclosure herein, the procedure zone comprises a zone on the catheter where a procedure may be initiated or accomplished. Thus, it may comprise an opening in the side wall of the catheter, a distal opening on an outer sleeve which terminates proximally to the distal end of the catheter, or a device or structure carried by the catheter which is operable to initiate or conduct a therapeutic or diagnostic procedure.

The method additionally comprises the step of advancing the catheter antegrade, in one implementation of the invention, through the mitral valve, through the aortic valve and into the aorta. This enables the procedure zone to be positioned upstream from the aortic valve, and allows the distal end of the flexible body to serve as an anchor to anchor and stabilize the catheter within the heart. A procedure may then be performed or initiated from the procedure zone on the catheter. Thus, the procedure zone is spaced proximally of the distal end a sufficient amount to allow the distal end of the catheter to anchor in an anatomical region of the heart or surrounding vasculature, such as, in this example, the left ventricular outflow tract.

The advancing step may comprise advancing the catheter along a previously positioned guidewire. The method may additionally comprise the step of allowing a flow directed catheter to flow through the mitral valve, through the aortic valve, and into the aorta, and thereafter advancing the guidewire through the flow directed catheter. The flow directed catheter may be removed, leaving the guidewire in place. Alternatively, the device catheter or catheters may be advanced along the flow directed catheter, such as where the flow directed catheter is a flow directed guidewire, or functions as a flow directed guidewire.

The advancing step may comprise advancing the catheter to position the procedure zone within a flow path between the mitral valve and the aortic valve.

The procedure may be a diagnostic procedure, or a therapeutic procedure. It may comprise an imaging procedure, or a hemodynamic monitoring procedure. The procedure may alternatively comprise an ablation procedure, recanalization procedure, drug delivery procedure, or any of a variety of tissue manipulation procedures, including valve repair procedures, such as an atrioventricular valve repair. For example, the procedure may comprise the step of grasping at least one leaflet of the mitral valve. The procedure may attach the anterior leaflet of the mitral valve to the posterior leaflet of the mitral valve.

In accordance with another aspect of the present invention, there is provided a method of orienting a first and second tissue grasper with respect to the mitral valve. The method comprises the steps of providing a catheter, having an elongate, flexible body, with a proximal end, a distal end, and first and second tissue graspers spaced apart from the distal end. The distal end of the catheter is transluminally advanced from the left atrium through the mitral valve and along the left ventricular outflow tract into the ascending aorta. The distal end of the catheter is positioned in the ascending aorta to stabilize and position the first and second tissue graspers, such that they are adjacent the mitral valve.

The method next comprises the step of extending at least the first tissue grasper radially outwardly from the flexible body. The extending step may comprise advancing the first tissue grasper from a first position in which a longitudinal axis of the tissue grasper extends generally parallel with the flexible body, to a second position in which the axis is inclined with respect to the flexible body. Depending upon the desired device construction, the axis of the tissue grasper may be inclined radially outwardly in a proximal direction, or radially outwardly in a distal direction. Alternatively, the extending step may comprise advancing the first tissue grasper distally along a pathway which is inclined with respect to a longitudinal axis of the catheter.

In accordance with another aspect of the present invention, there is provided a method of grasping a mitral valve leaflet. The method comprises the steps of providing a catheter having an elongate, flexible body, with a proximal end and a distal end. The distal end is transluminally advanced from the left atrium through the mitral valve and along the left ventricular outflow tract into the ascending aorta. In any of the procedures discussed herein, the catheter may enter the left atrium through any of the known transvascular or surgical pathways. A tissue grasper may be then deployed from a position on the catheter, spaced apart from the distal end. A mitral valve leaflet is grasped using the tissue grasper. Depending upon the tissue grasper configuration, the grasping step may comprise piercing the leaflet, trapping the leaflet, applying suction to the leaflet, or other tissue grasping technique.

In accordance with another aspect of the present invention, there is provided a method of performing an atrioventricular valve repair. The method comprises the steps of providing a catheter having an elongate flexible body, with a proximal end, a distal end, and at least one leaflet grasper thereon. The distal end is transluminally advanced from the left atrium, through the mitral valve and along the left ventricular outflow tract into the ascending aorta. At least a first leaflet of the mitral valve is grasped with the leaflet grasper, and the first leaflet is secured to at least one other anatomical structure. In one implementation of the invention, the first leaflet is secured to a second leaflet. Alternatively, the first leaflet may be secured to a valve annulus. The securing step may comprise advancing a suture through the first leaflet. Alternatively, the securing step may comprise attaching a clip to the first leaflet. The securing step may alternatively comprise attaching a tissue anchor to the first leaflet.

In accordance with a further aspect of the present invention, there is provided a method of orienting a catheter with respect to the mitral valve. The method comprises the steps of positioning a guidewire from the left atrium through the mitral valve and along the left ventricular outflow tract into the ascending aorta. A catheter is advanced along the guidewire, the catheter having an anchor and a procedure site. The anchor is located with respect to an anatomical feature, such that the procedure site is at a predetermined orientation with respect to the mitral valve. The positioning step may include the use of a flow directed structure. The locating the anchor step may comprise positioning a distal portion of the catheter within the ascending aorta. The locating the anchor step may comprise positioning the catheter such that it is approximately centered on the posterior leaflet of the mitral valve.

The methods and devices of the present invention may be configured to access either the right side or the left side of the heart. In general, a right side procedure involves advancing the catheter from the right atrium through the right ventricle and into the pulmonary artery. The catheter is anchored in the pulmonary artery, along the right ventricle outflow tract. Right side positioning enables procedures to be performed on the tricuspid or pulmonic valve, as will be apparent to those of skill in the art in view of the disclosure herein, utilizing procedures and devices disclosed elsewhere herein, except that the right side procedures will not require a transseptal crossing. Access for any of the procedures described herein could be by way of a puncture in the left ventricle, left atrium, aorta, or right atrium for off pump valve repair in an open surgery.

Thus, in accordance with another aspect of the present invention, there is provided a method of performing a procedure in the heart. The method comprises the steps of providing a catheter having an elongate flexible body, a proximal end, a distal end, and a procedure zone spaced proximally apart from the distal end. The catheter is advanced through the right atrium, through the right ventricle, and into the pulmonary artery, such that the procedure zone is positioned at a treatment site. A procedure may thereafter be performed from the procedure zone. In one application of the invention, the procedure is performed on the tricuspid valve. Alternatively, the procedure may be performed on the pulmonic valve. The advancing step may comprise advancing the catheter to a position such that the distal end of the catheter is within the right ventricle outflow tract of the pulmonary artery.

In accordance with another aspect of the present invention, there is provided a method of performing a procedure in the heart. The method comprises the steps of providing a catheter, having an elongate flexible body, a proximal end, a distal end, and a procedure zone spaced proximally apart from the distal end. The catheter is advanced through at least two valves in the heart, through a first chamber in the heart and at least into and in some implementations through a second chamber in the heart. This enables positioning of the procedure zone adjacent or in the proximity of a desired treatment site. A procedure is thereafter performed from the procedure zone. In one application of the invention, the advancing the catheter step comprises advancing the catheter through both the mitral valve and the aortic valve. The procedure may comprise a valve repair.

As discussed previously herein, the present invention also provides a variety of catheters, for performing the procedures disclosed herein. In accordance with one aspect of the present invention, there is provided a catheter for accessing the heart. The catheter comprises an elongate flexible body, having a proximal end and a distal end. The distal end includes an anchor zone AZ (e.g., as in FIGS. 3A and 4-12). At least one tissue manipulator is carried by the flexible body, proximally of the anchor zone AZ.

In general, the anchor zone is of a sufficient length distally of the procedure zone, to enable orientation and anchoring of the catheter within the vasculature. In one embodiment, the minimum length of the anchor zone is at least about 3 cm. In some embodiments, the anchor zone is at least about 5 cm, and in certain applications, at least about 10 cm in length.

The tissue manipulator may be movable between an axial orientation or transluminal navigation and an inclined orientation for manipulating tissue. In certain embodiments, the catheter may comprise a first and a second tissue manipulator. The tissue manipulator may comprise a tissue grasper for grasping a heart valve leaflet. In many embodiments, the catheter comprises at least a first component which is axially movable with respect to a second component, to manipulate tissue such as to grasp and secure opposing leaflets on a valve.

Although the present invention has been disclosed with reference to certain specific embodiments of devices and methods, the inventors contemplate that the invention more broadly relates to methods disclosed above, such as those useful for orienting a catheter with respect to an anatomical structure, as well as performing diagnostic and/or therapeutic procedures in the heart or adjacent the heart. Accordingly, the present invention is not intended to be limited to the specific structures and steps disclosed herein, but rather by the full scope of the attached claims.

What is claimed is:

1. A catheter, comprising:
an elongate flexible body, having a proximal end and a distal end, the elongate flexible body having housed therein a fastening material configured to suture two heart leaflets together;
an anchor zone on a distal portion of the flexible body;
a first tissue manipulator and a second tissue manipulator carried by the catheter proximally of the anchor zone, the tissue manipulators being capable of being moved independently of each other and having a fixed end and a free end, the free ends being moveable to an extended position in which the free ends are proximal of the fixed ends, the tissue manipulators being disposed in the extended position such that an angle of not more than 90 degrees is defined between a portion of the elongate flexible body disposed proximally of the fixed ends and an adjacent portion of each of the tissue manipulators facing the portion of the elongate flexible body disposed proximally of the fixed ends;
a first receptacle located within the first tissue manipulator for receiving a first fixating member;
a second receptacle located within the second tissue manipulator for receiving a second fixating member; and
a first end of a fastening material disposed within the first receptacle and a second end of the fastening material is disposed within the second receptacle;
wherein a portion of the elongate flexible body located proximal of the tissue manipulators is sufficiently flexible and has sufficient length to enable the tissue manipulators to be advanced from a peripheral venous or arterial blood vessel to a left atrium of a heart, and through a mitral valve of the heart;
wherein the distal portion is configured to extend at least into an anatomical region adjoining the heart valve and the anchor zone is configured to orient and anchor the catheter so that the tissue manipulators can be positioned at the valve.

2. A catheter as in claim 1, wherein the minimum length of the anchor zone on the distal side of the tissue manipulator is at least about 3 cm.

3. A catheter as in claim 1, wherein the minimum length of the anchor zone on the distal side of the tissue manipulator is at least about 5 cm.

4. A catheter as in claim 1, wherein the minimum length of the anchor zone on the distal side of the tissue manipulator is at least about 10 cm.

5. A catheter as in claim 1, wherein the tissue manipulator is moveable between an axial orientation for transluminal navigation and an inclined orientation for manipulating tissue.

6. A catheter as in claim 1, wherein the first tissue manipulator comprises a tissue grasper for grasping a heart valve leaflet.

7. A catheter as in claim 1, comprising at least a first component which is axially moveable with respect to a second component.

8. The catheter as in claim 1, wherein the distal portion is configured to extend from a left atrium, through a mitral valve and into a left ventricular outflow tract.

9. The catheter as in claim 1, wherein the distal portion is configured to extend through a left ventricular outflow tract into an aorta.

10. The catheter as in claim 1, wherein the distal portion is configured to extend through a tricuspid valve and into a right ventricular outflow tract.

11. The catheter as in claim 1, wherein the distal portion is configured to extend through a right ventricular outflow tract into a pulmonary artery.

12. The catheter as in claim 1, wherein the first tissue manipulator is asymmetric to the second tissue manipulator.

13. The catheter as in claim 12, wherein the first tissue manipulator is longer than the second tissue manipulator.

14. A catheter as in claim 1, wherein the tissue manipulator comprises a first elongate tissue manipulator having a first length and a second tissue manipulator having a second length, the first and second tissue manipulators both configured to engage portions of a heart valve from the same side of the valve, the second length being greater than the first length.

15. A catheter as in claim 1, wherein the first and second tissue manipulators are capable of sequential deployment.

16. A catheter as in claim 1, wherein the shape of the catheter acts as a fulcrum about which the catheter can be manipulated with respect to the individual valve leaflets.

17. A catheter system as in claim 1, wherein at least one of the first and second tissue manipulators is configured to self-deploy to the extended position from a retracted position, wherein the retracted position is suitable for transluminal advancement.

18. A catheter system as in claim 17, wherein at least one of the first and second tissue manipulators is coupled with a hinge comprising stored energy when the tissue manipulator coupled therewith is in the retracted position.

19. A catheter system as in claim 17, wherein the catheter system comprises a structure for restraining the tissue manipulators in the retracted position during transluminal advancement.

20. A catheter system as in claim 19, wherein the catheter system comprises an actuator for providing relative movement between the restraining structure and the elongate body, wherein in a first position the restraining structure maintains the tissue manipulators in the retracted position and a second position the restraining structure permits at least one of the tissue manipulators to self-deploy.

21. A catheter system as in claim 20, wherein the actuator provides for relative movement to a third position in which the restraining structure permits the first and the second tissue manipulators to self-deploy.

* * * * *